US00PP36708P2

(12) United States Plant Patent
Harrell

(10) Patent No.: US PP36,708 P2
(45) Date of Patent: May 27, 2025

(54) ***THUJA* PLANT NAMED 'CFNI'**

(50) Latin Name: ***Thuja plicata* X *Thuja standishii***
Varietal Denomination: CFNI

(71) Applicant: Paul R. Harrell, Jackson, NC (US)

(72) Inventor: Paul R. Harrell, Jackson, NC (US)

( * ) Notice: Subject to any disclaimer, the term of this patent is extended or adjusted under 35 U.S.C. 154(b) by 0 days.

(21) Appl. No.: 18/946,485

(22) Filed: Nov. 13, 2024

(51) Int. Cl.
*A01H 5/00* (2018.01)
*A01H 7/00* (2006.01)

(52) U.S. Cl.
USPC ..... Plt./213

(58) Field of Classification Search
USPC ..... Plt./213
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Thuja* named 'CFNI' that is characterized by its vigorous growth habit as a young plant with the growth rate decreasing after 3 to 5 years, its full and dense foliage with little or no shearing, its strong central leader, its vertically oriented foliage sprays, and its dwarf to semi-dwarf plant habit.

2 Drawing Sheets

Botanical classification: *Thuja plicata* X *Thuja standishii.*
Varietal denomination: 'CFNI'.

BACKGROUND OF THE INVENTION

The present invention relates to a new and distinct cultivar of *Thuja plicata* X *Thuja standishii* and will be referred to hereafter by its cultivar name, 'CFNI'. 'CFNI' represents a new cultivar of arborvitae, an evergreen tree grown for landscape use.

The Inventor discovered 'CFNI' as a naturally occurring branch mutation of *Thuja* 'Green Giant' (not patented) that was growing outdoors in a field plot at a nursery in Spring of 2015 in Jackson, North Carolina.

Asexual propagation of the new cultivar was first accomplished by one of the Inventors using stem cuttings in Jackson, North Carolina in January of 2017. Asexual propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'CFNI' as a unique cultivar of *Thuja.*

1. 'CFNI' exhibits a vigorous growth habit as a young plant with the growth rate decreasing after 3 to 5 years.
2. 'CFNI' exhibits full and dense foliage with little or no shearing.
3. 'CFNI' exhibits a strong central leader.
4. 'CFNI' exhibits vertically oriented foliage sprays.
5. 'CFNI' exhibits a dwarf to semi-dwarf plant habit.

The parent plant of 'CFNI' differs from 'CFNI' in having a larger plant height (twice the size), a faster growth rate, a less dense growth habit, and leaf sprays that are held more horizontal. 'CFNI' can be most closely compared to the *Thuja* cultivar 'BFC68' (U.S. Plant Pat. No. 26,684) and 'T p x T s Junior Giant' (U.S. Plant Pat. No. 31,297). 'BFC68' is similar to 'CFNI' in plant shape. 'BFC68' differs from 'CFNI' in having a less dense growth habit, a larger plant size, and branches and leaves that are held more horizontal. 'T p x T s Junior Giant' is similar to 'CFNI' in having a compact plant habit and in plant shape. 'T p x T s Junior Giant' differs from 'CFNI' in having a slower growing plant rate and darker green foliage.

BRIEF DESCRIPTION OF THE DRAWINGS

The accompanying color photographs illustrate the overall appearance and distinct characteristics of the new *Thuja*. The photographs were taken of a four-year-old plant as grown outdoors in a production field in Jackson, North Carolina.

The photograph in FIG. 1 provides an overall view of the plant habit of 'CFNI'.

Figure 1:
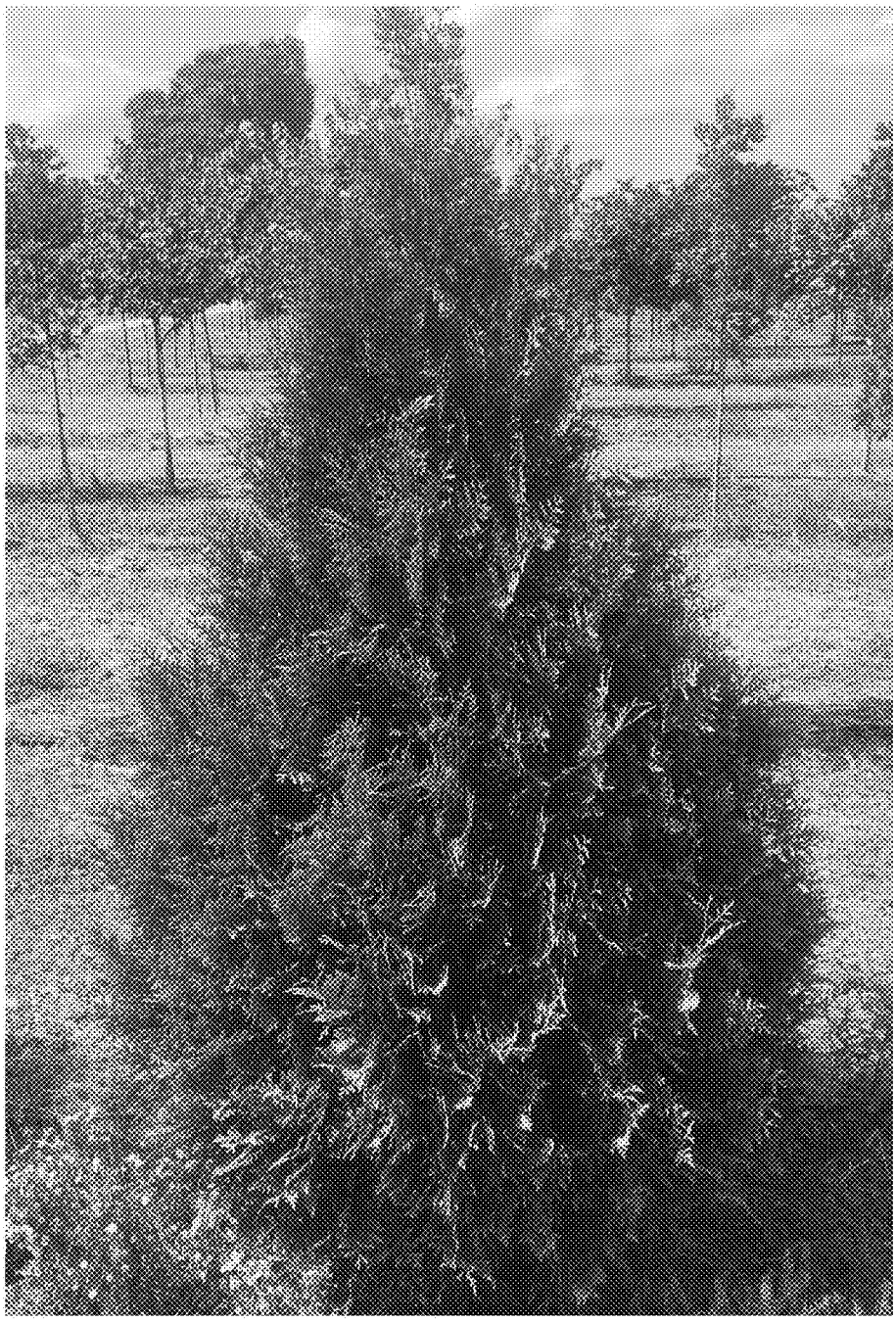
Figure 2:
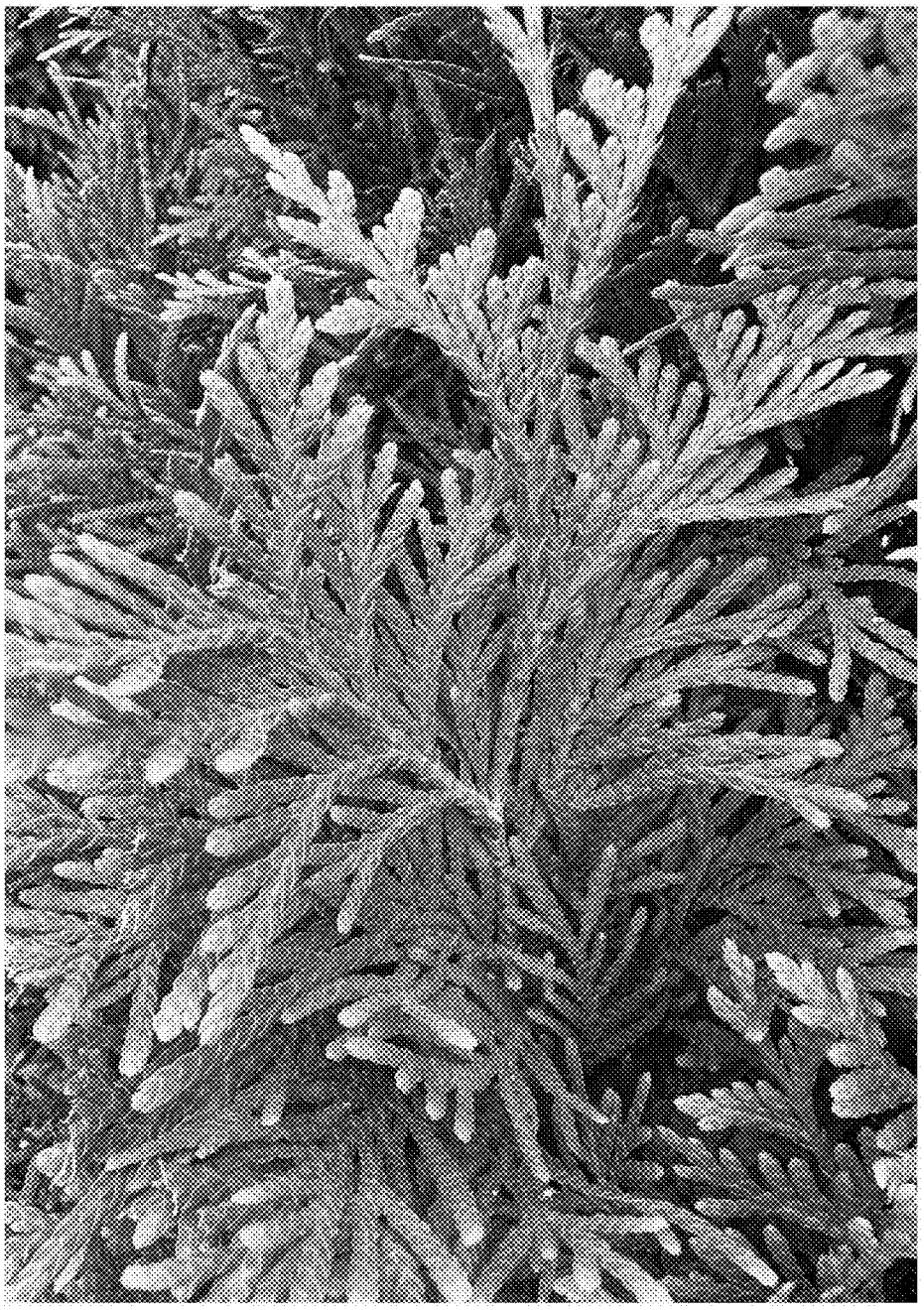

The photograph in FIG. 2 provides a close-up view of the foliage of 'CFNI'.

The colors in the photographs are as close as possible with the photographic and printing technology utilized and the color values cited in the detailed botanical description accurately describe the colors of the new *Thuja.*

DETAILED BOTANICAL DESCRIPTION

The following is a detailed description of the new cultivar as taken from three-year-old plants as grown outdoors in 3-gallon containers in Park Hill, Oklahoma. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Coniferous, evergreen tree.

*Plant habit*.—Conical, upright, dense and compact with sprays orientated vertically.

*Plant size*.—Dwarf to semi-dwarf, reaches an average of 1.5 m in height and 80 cm in width as a 3-year-old plant in a container, reaches up to 4.6 m in height and 3 m in width as a mature plant in the landscape.

*Hardiness*.—At least in U.S.D.A. Zones 5 to 7.

*Diseases and pests*.—No resistance or susceptibility to diseases or pests has been observed.

*Root description*.—Fibrous, moderately branched, moderately thick, 175A in color.

*Propagation*.—Stem cuttings.

*Growth rate*.—Vigorous growth habit for the first 3 years, then slowing to moderate.

*Root development*.—Roots initiate in 8 weeks, a fully rooted young plant is produced in 12 months from a rooted cutting.

Branch description:

*Branch quantity*.—Average of 700 branches from main stem, with an average of 10 branches per lateral branch.

*Branch shape*.—Young; flattened, mature; rounded.

*Branch size*.—Main branch; 4 cm in width, 1.2 m in length, lateral branches; 40 cm in length and 5 mm in diameter, tertiary branches; 19 cm in length, 3 mm in width.

*Branch surface*.—Densely covered with scale-like leaves that are matte, scale-like leaves; whorled in group of 2 to 3 leaves per whorl, 10 per 2 cm section, average of 3.5 mm in length, 3 mm in width, sharp acuminate apex, young surfaces are slightly glossy and glabrous, mature surfaces and bark is matte, rugose, and exfoliating.

*Branch arrangement*.—Alternate.

*Branch strength*.—Strong.

*Internode length*.—Average of 1.5 cm.

*Branch color*.—Young branches; 145A, mature branches; 165A, older bark; 200A.

Foliage description:

*Leaf arrangement*.—Alternate.

*Leaf attachment*.—Sessile.

*Leaf shape*.—Linear, scale-like.

*Leaf division*.—Simple.

*Leaf base*.—Cuneate.

*Leaf apex*.—Short apiculate.

*Leaf venation*.—Not distinguishable, coloration matches leaf coloration.

*Leaf margins*.—Entire.

*Leaf fragrance*.—When crushed, scale-like leaves produce a very strong pleasant smell typical fragrance of *Thuja*.

*Leaf surface*.—Upper and lower surfaces; glabrous and glossy.

*Leaf color*.—Immature upper and lower surface; 145A, mature upper and lower surface; 137B.

*Leaf size*.—Average of 15 cm in length and 6 mm in width.

*Leaf quantity*.—Average of over 8,000 scale-like leaves per branch.

*Leaf glands*.—Average of 0.5 mm in diameter, orbicular in shape, matches leaf color surfaces.

Cone description: Neither male nor female cones have been observed to date.

It is claimed:

1. A new and distinct cultivar of *Thuja* plant named 'CFNI' as herein illustrated and described.

* * * * *